United States Patent [19]

Kim

[11] Patent Number: 5,765,559
[45] Date of Patent: Jun. 16, 1998

[54] MULTI-CUFFED ENDOTRACHEAL TUBE AND METHOD OF ITS USE

[75] Inventor: Young Hwa Kim, Woodbury, Minn.

[73] Assignee: Higher Dimension Research, Inc., Woodbury, Minn.

[21] Appl. No.: 637,396

[22] Filed: Apr. 25, 1996

[51] Int. Cl.$^6$ .................................................. A61M 29/00
[52] U.S. Cl. ...................................... 128/207.15; 606/191
[58] Field of Search ................................. 606/191, 194, 606/195, 192, 1; 604/96–101; 128/200.26, 207.15, 898

[56] References Cited

U.S. PATENT DOCUMENTS

| | | |
|---|---|---|
| 4,423,725 | 1/1984 | Baran et al. ..................... 604/101 |
| 4,567,882 | 2/1986 | Heller . |
| 4,681,094 | 7/1987 | Rolnick . |
| 4,744,366 | 5/1988 | Jang . |
| 4,763,654 | 8/1988 | Jang . |
| 4,793,327 | 12/1988 | Frankel . |
| 4,832,020 | 5/1989 | Augustine . |
| 4,976,216 | 12/1990 | Gluck . |
| 5,033,466 | 7/1991 | Weymuller . |
| 5,095,888 | 3/1992 | Hawley . |
| 5,174,283 | 12/1992 | Parker . |
| 5,178,132 | 1/1993 | Mahefky . |
| 5,184,603 | 2/1993 | Stone . |
| 5,203,320 | 4/1993 | Augustine . |
| 5,285,777 | 2/1994 | Beckwith ..................... 128/207.15 |
| 5,287,848 | 2/1994 | Cubb et al. . |
| 5,315,992 | 5/1994 | Dalton . |
| 5,318,021 | 6/1994 | Alessi . |
| 5,328,471 | 7/1994 | Slepian ..................... 604/101 |
| 5,361,753 | 11/1994 | Pothman et al. . |
| 5,406,941 | 4/1995 | Roberts . |
| 5,447,152 | 9/1995 | Kohsai et al. ..................... 128/207.15 |

OTHER PUBLICATIONS

Terblanche, et al., The New England J. of Medicine, vol. 320, #21, May 25, 1989, pp. 1393–1398.

Clinical Procedures in Anesthesia and Intensive Care, edited by Jonathan L. Benumof, published by J. B. Lippincott Company (Book).

Complications and Consequences of Endotracheal Intubation and Tracheostomy, by J.L. Stauffer, D.E. Olson, and T.L. Petty, published in the American Journal of Medicine, 1981.

*Primary Examiner*—Michael Buiz
*Assistant Examiner*—William Lewis
*Attorney, Agent, or Firm*—Malcolm Reid

[57] ABSTRACT

A plurality of cuff rings for an endotracheal tube for intubation of a trachea. At least one of the cuff rings is inflatable and deflatable independent of the other cuff ring so that at least one of the cuff rings may always remain inflated to maintain an airtight seal between the cannula of the endotracheal tube and a patient's trachea. Each cuff ring is successively inflated and deflated during the period the endotracheal tube is in a patient's trachea, thereby intermittently relieving the trachea of pressure on its inner wall. The intermittent relief of pressure by periodic deflation of each cuff ring reduces damage to the trachea. The cuff rings each have a surface associated therewith to lubricate the area of the trachea in contact with the cuff ring to substantially reduce the occurrence of damage to the trachea from abrasion by the cuff rings.

3 Claims, 9 Drawing Sheets

MULTI-CUFFED ENDOTRACHEAL TUBE AND METHOD OF ITS USE

FIELD OF THE INVENTION

The present invention relates generally to a multi-cuffed endotracheal tube for intubation of a trachea. The multi-cuffed endotracheal tube relieves a trachea of the constant pressure exerted against it by the cuff of a conventional endotracheal tube when inserted into a patient's trachea either through the mouth, nose, or a tracheostomy. The invention also relates to a method of successive cycles of pressurization and depressurization of portions of a trachea during the course of an intubation procedure. It also relates to a method of lubricating the interface between the cuff and the inner wall of the trachea.

BACKGROUND ART

Endotracheal intubation is an established procedure used to assure a patient's open airway during surgical procedures requiring general anesthesia. Intubation of the trachea also protects the airway from gastric contents, allows positive air pressure to be administered to the lungs, and permits suctioning of the tracheobronchial tree for removal of secretions. Intubation is indicated for the awake patient in respiratory failure or impending respiratory failure. The endotracheal tube is generally inserted through a patient's mouth or nose and then into the trachea, but may also be directly inserted into the trachea through a tracheostomy.

Figure 1A:
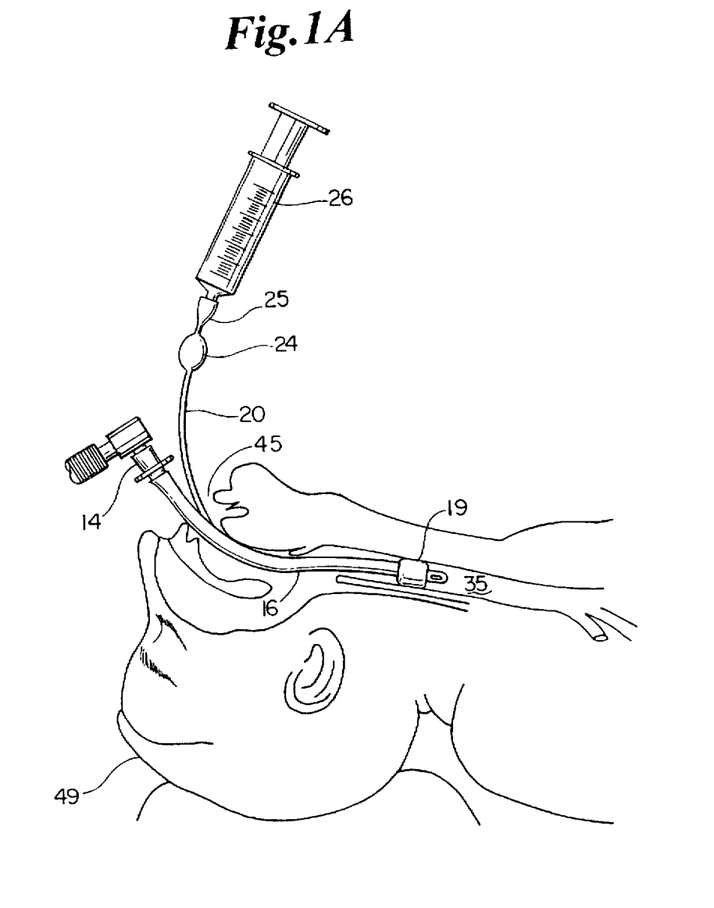
FIG. 1A is a pictorial diagram of a conventional endotracheal tube in the trachea of a patient with the cuff inflated.
Figure 1B:
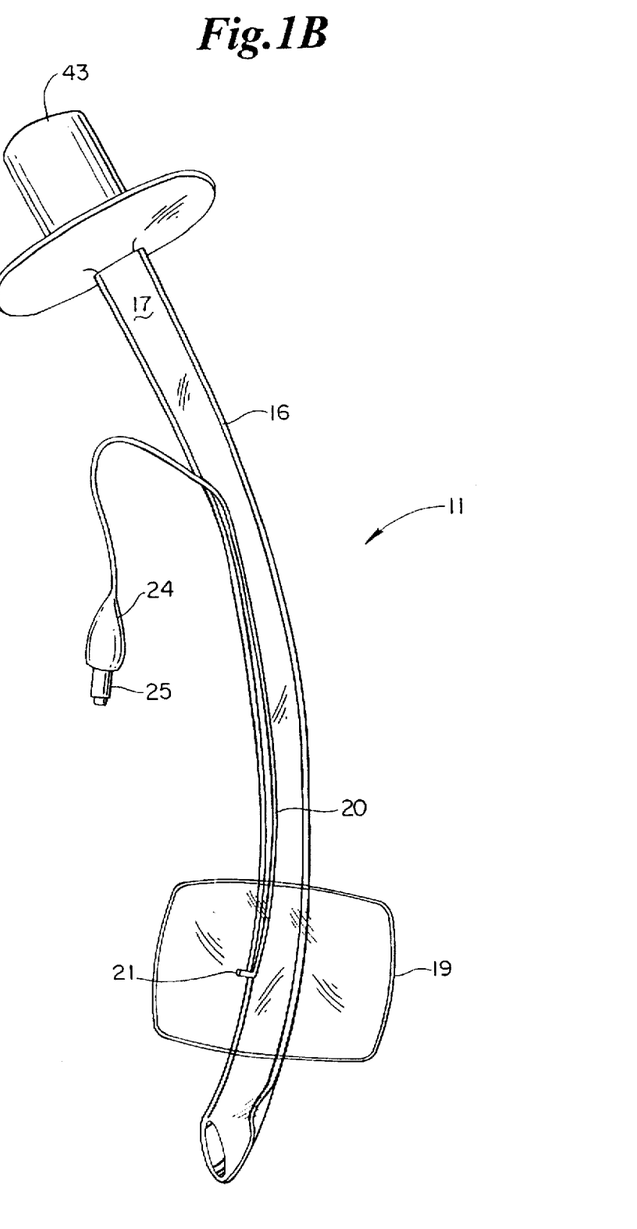
FIG. 1B is a pictorial diagram of a conventional endotracheal tube outside the patient with the cuff inflated.
Figure 2:
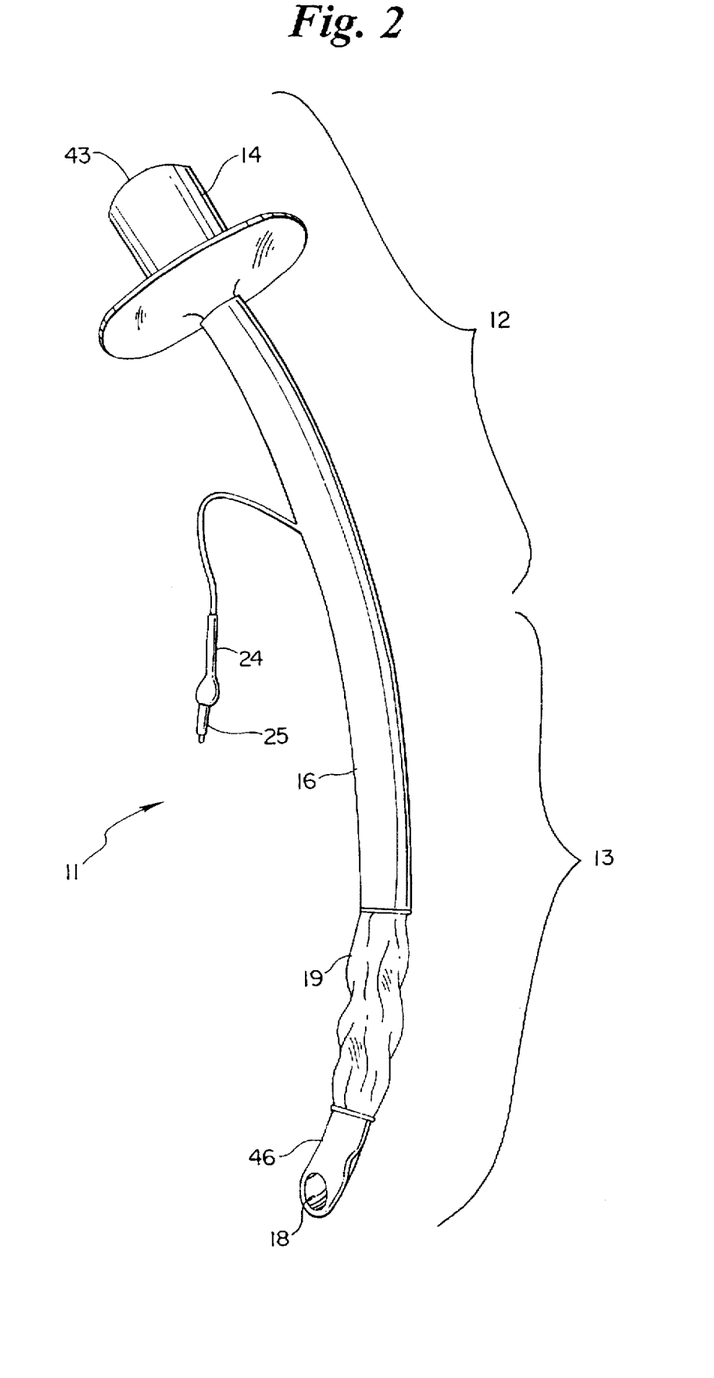
FIG. 2 is a pictorial diagram of a conventional endotracheal tube before emplacement in a patient with the cuff deflated.

Cuffed endotracheal tubes 11 are generally constructed of bio-compatible polyvinyl chloride and a low pressure, high volume cuff 19 as shown in FIG. 1A and 1B. FIG. 1A shows the endotracheal tube 11 inserted through the patient's mouth and into the patient's trachea 35 with the cuff 19 in an inflated state as it would be during a surgical procedure. While not shown in FIG. 1A, the endotracheal tube can also be inserted through a tracheostomy. FIG. 1B depicts the endotracheal tube 11 outside the patient's trachea 35 with the cuff 19 inflated. FIG. 2 shows the endotracheal tube 11 outside the patient. It shows the endotracheal tube 11 with the cuff 19 in a deflated state as the cuff would be when removed from its sterile packaging. The endotracheal tube 11 is in a deflated state when not in situ in a patient. As shown in FIGS. 1A, 1B and 2, an endotracheal tube 11 consists of a cannula 16 having a distal end 13, and a connector 14 at the proximal end 12. The endotracheal tube 11 allows air to be forced into the lungs of a patient from the connector orifice 43 through the cannula 16 to the distal end 13 of the cannula 16. The cannula 16 near the distal end 13 is surrounded by the cuff 19. The cuff 19 is bonded to the cannula 16 circumferentially at both ends of the cuff 19 to provide an air tight seal. The cannula 16 is provided with at least one cuff port 21 on that portion of the cannula 16 interior to the cuff 19. The cuff port 21 is connected to the cuff inflation line 20 which extends from the cuff port 21 to beyond the connector 14 to provide adequate length for the physician to attach a syringe 26 to the end of the cuff inflation line 20 protruding from the patient's mouth, nose, or from a tracheostomy. That portion of the endotracheal tube 11 protruding from the patient's mouth, nose, or a tracheostomy has affixed to it a valve 25 which is normally closed; opening only when air is injected into it by the syringe 26 or suctioned out by the syringe 26. The valve 25 allows air to be forced into the cuff inflation line 20 by pushing the piston into the cylinder of the attached syringe 26, but will not allow the air to escape unless the syringe piston is retracted. Upon forcing air into the cuff inflation line with the syringe 26, the air enters the cuff 19 through the cuff port 21 and thereby inflates the cuff 19. The pilot balloon 24 indicates inflation of the cuff 19 when the pilot balloon 24 is inflated.

As previously mentioned and as FIGS. 1A and 1B illustrate, after insertion of the endotracheal tube 11 into the patient's trachea 35, the cuff 19 is inflated to conform to the natural shape of the trachea 35 providing a relatively air tight seal between the endotracheal tube 11 and the trachea 35.

A complete description of the techniques of insertion of an endotracheal tube 11 and use thereof is beyond the scope of this specification. For details of endotracheal use, see Clinical Procedures in Anesthesia and Intensive Care, edited by Jonathan L. Benumof and published by J. B. Lippincott Company.

Endotracheal intubation efficacy is well accepted. High-volume, low-pressure cuffs, now widely used, have decreased morbidity from intubation. However, serious adverse consequences from intubation still exist, particularly from prolonged use. One study reported tracheal stenosis in 19% of patient's that underwent prolonged tracheal intubation and in 65% that had undergone a tracheostomy. Some damage may be so severe that a portion of the trachea may have to be removed. See Complications and Consequences of Endotracheal Intubation and Tracheostomy, by Stauffer J. L., Olson D. E., and Petty, T. L., published in the American Journal of Medicine, 1981.

The damage is due to the constant pressure exerted by the cuff 19 on the tracheal wall, especially during prolonged surgery, as well as the abrasion of the trachea by the cuff 19. The constant pressure of the cuff on the delicate tracheal wall may damage the fine hair-like cilia lining the wall or may cut off the blood flow to the surface tissue of the trachea to such a degree that tissue necrosis results. The constant cuff 19 contact can also result in bacteria build-up at the trachea-cuff margin, resulting in infection of that portion of the trachea and beyond. While, prolonged surgeries present a high and unacceptable risk of damage to the trachea, intubation of the comatose patient with non functional lungs presents an even higher risk. With these patients, the cuff of the endotube is typically inflated for days. The only relief being the short period occurring once every few days when hospital staff replaces the endotracheal tube with a new one. Since these patients require constant ventilation, there is little choice, but to constantly keep the airway sealed.

It would be advantageous to combine an endotracheal tube 11 with a cuff 19 that automatically inflated and deflated at periodic intervals and yet maintained a constant air-tight seal between the endotracheal tube 11 and the trachea 35. It is also desirable to reduce the potential of tracheal damage caused by the conventional endotracheal tube 11 by reducing friction between the cuff 19 and the trachea 35. Reduction of the constant pressure of the cuff against the trachea and friction of the cuff against the trachea results in a more normal blood flow with resulting reduction of necrosis of the trachea 35.

The cuff of the present invention is illustrated and discussed primarily in combination with a cannula for endotracheal intubation of human patients. However, the multi-cuff of the present invention may also be used in combination with a cannula for intubation of the trachea of animals as well as humans.

SUMMARY OF THE INVENTION

Figure 3:
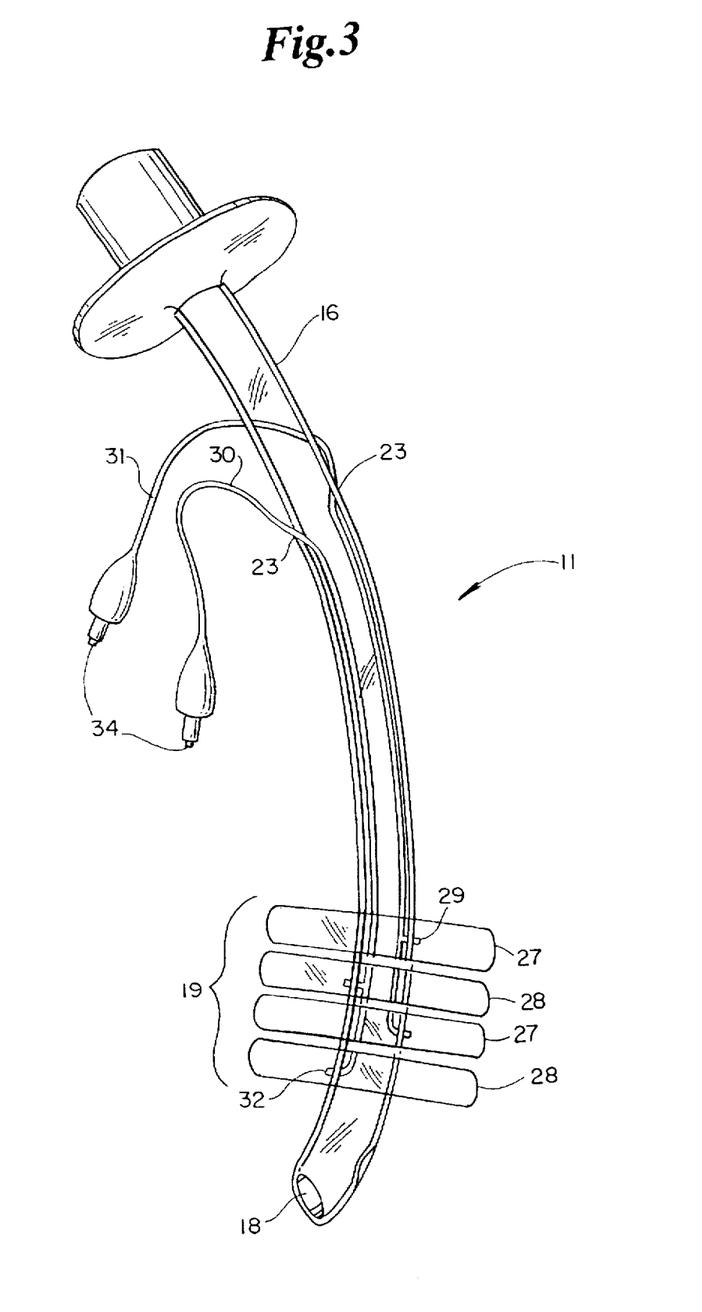
FIG. 3 is a pictorial diagram of the endotracheal tube of the present invention with the cuff rings inflated.

Accordingly, it is a primary object of the present invention to provide an endotracheal tube with a cuff 19 having a plurality of cuff rings 27 as shown in FIG. 3, each of which are capable of being inflated and deflated periodically with at least one of the cuff rings 27 remaining inflated while others are deflated. This allows for accomplishment of the primary objective of the endotracheal tube cuff 19, which is to seal off the area surrounding the endotracheal tube 11 between the tube 11 and the trachea 35. It also satisfies the objective of eliminating or substantially reducing damage to the tracheal wall resulting from constant pressure on the delicate tissue of the trachea 35 due to pressure of the inflated cuff 19 on the trachea 35 during a lengthy medical procedure or during ventilation of a patient while comatose.

A further objective of the present invention is accomplished by providing a means of lubricating the contact point between the cuff 19 and the trachea 35. Damage due to frictional abrasion between the tracheal wall 35 and the cuff 19 is thereby reduced. Frictional abrasion is caused by movement of the endotracheal tube 11 in the trachea 35 by medical personnel during the medical procedure requiring intubation.

Yet another objective of the invention is accomplished by introducing an amount of an antibiotic in a lubricating means 33 to help fight bacterial growth that is a natural concomitant of a foreign object in the trachea 35, a relatively immobile trachea due to the general anesthetic administered to the patient, and the reduced wave-like motion of the cilia due to the pressure of the cuff rings 27 against the trachea 35.

An additional objective of the present invention is to provide a means of limiting higher than acceptable pressure of the cuff against the tracheal wall caused by momentary over-inflation of the cuff rings 27 due to minor fluctuations in the regulated air supply 34 used to deliver the air pressure to the cuff rings 27 or an incorrect air pressure setting. This is accomplished by cuff rings 27 that are formed at an angle to the longitudinal axis 44 of the cannula 16. As the air pressure exceeds a certain prescribed upper limit, the combination of the strength of the material comprising the cuff rings 27 and the angle at which the cuff rings 27 contact the trachea 35 allow the cuff rings 27 to deform and cover a larger surface area of the trachea 35, thereby reducing the pressure per unit of surface area of the trachea 35.

Still another objective of the present invention is to keep the airway above the cuff 19 or the cuff rings 27 free from fluid and other biological debris. The present invention provides a means for suctioning off this matter as needed.

A further objective of the present invention is to provide a cuff which maintains a constant seal between the trachea, whether human or other animal, and an inserted cannula without damaging the tracheal tissue due to uninterrupted pressure of the cuff on the tracheal wall.

DETAILED DESCRIPTION OF THE INVENTION

Reference is now made to FIGS. 1A and 1B of the drawings showing a conventional endotracheal tube 11. The tube consists of a proximal end 12 and a distal end 13. The proximal end 12 is terminated in a connector 14 for connection to a regulated breathable air supply pump 15 for introduction of gases to the patient's 49 lungs to maintain positive pressure in the lungs to assist the patient 49 to breathe during the medical procedure being administered during endotracheal intubation. The endotracheal tube 11, which extends from the patient's mouth 45 and into the trachea 35 is in the form of a cannula 16 having an open longitudinally extending interior referred herein as the lumen 17. The cannula 16 is open at the distal end 13 forming the distal opening 18. The distal opening 18 is often formed at an acute angle to the longitudinal axis of the cannula 16 rather than at a right angle to provide a larger open area and allow more easy machining of a soft rounded edge on the distal opening 18. The larger area of the distal opening 18 helps to avoid obstruction of the lumen 17 while the rounded edge is meant to avoid tearing of the tissue through which the cannula 16 passes upon insertion of the endotracheal tube 11 into the patient. The narrow pointed cannula end 46 also allows the cannula 16 to work its way through portions of the patient's larynx 47, pharynx 48, and trachea 35 that may be partially closed off. The cannula 16 is generally constructed of radio-opaque bio-compatible polyvinyl chloride tubing having some small degree of flexibility.

As further shown in FIG. 1, the distal end 13 is surrounded by a low pressure high volume cuff 19. FIGS. 1A and 1B show the cuff 19 in a fully inflated state. FIG. 2 shows a conventional endotracheal tube 11 with the cuff 19 in a deflated state. The cuff 19, like the cannula 16, is generally constructed of radio-opaque bio-compatible polyvinyl chloride, but of a very thin wall. The thin wall allows for inflation and deflation. When the cuff 16 is inflated, the cuff 16 conforms to the natural shape of the trachea 35 while providing the required seal by contact with the minimal area of tracheal wall. The cuff 16 is both inflated and deflated through the cuff inflation line 20 which extends from the cuff port 21 to outside of the patient's mouth. The cuff port 21 is a transverse opening in the side wall of the cannula 22 allowing communication from the lumen 17 to the inside of the cuff 19. The cuff inflation line 20 is attached to the cuff port 21 using conventional bonding techniques. The inside diameter of the cuff inflation line 20 is usually the same as the diameter of the cuff port 21. The cuff inflation line 20 is bonded to the inside wall of the cannula 22 and exits the cannula near the connector 14 through the inflation line port 23. At the terminus of the proximal end of the cuff inflation line 20, a pilot balloon 24 is connected to indicate cuff 19 inflation. A valve 25 attaches to the pilot balloon 24 and in turn is adapted to connect to a syringe 26 for expression of air into the cuff 19 or deflation of the cuff 19. The valve 25 allows air to be expressed into the cuff inflation line 20, but closes so air is not allowed out. However, air can be suctioned out of the cuff inflation line 20 by the back pressure on the valve 25, which causes the valve 25 to open when the syringe plunger is pulled out of the syringe 26.

The conventional endotracheal tube 11 is inserted into the patient's mouth or nose, extended through the pharynx 48, then the larynx 47, and into the trachea 35. The tube 11 is long enough that the connector 14 extends beyond the patient's mouth while the distal end 13 of the tube 11 is in the trachea 35. After insertion of the endotracheal tube 11 in the patient, the connector 14 is connected to a breathable air supply pump 15 and a positive pressure is maintained in the lungs by passage of the air through the connector orifice 43, through the lumen 17, out the distal opening 18, and into the trachea 35. Prior to applying positive pressure to the lungs, medical staff inflates the cuff 19 by compressing air in the syringe 26 through the cuff inflation line 20. When the cuff 19 is inflated, the cuff 19 conforms to the natural shape of the trachea while providing a seal with the trachea wall.

During the medical procedure requiring intubation, the cuff 19 must be inflated at all times for maximum effectiveness. Long duration of inflation results in damage to the trachea as discussed previously in this specification.

FIG. 3 illustrates an endotracheal tube 11 of the present invention in the trachea of a patient with cuff rings 27 and 28 of the present invention inflated. The cuff 19 of the present invention is segmented into a plurality of cuff rings 27 and 28. The cuff rings 27 and 28 are divided into distal cuff rings 28 and proximal cuff rings 27. Each of the cuff rings 27 and 28 axially surrounds the cannula 16. Each cuff ring 27 and 28 is in communication with the lumen 17 by either a distal cuff port 22 or a proximal cuff port 19, respectively. In the embodiment shown in FIG. 3, all of the distal cuff rings 28 are connected to a common inflation line referred to as the distal cuff ring inflation line 30. All of the proximal cuff rings 27 are connected to a common inflation line referred to as the proximal cuff ring inflation line 31. The distal and proximal cuff ring inflation lines 30 and 31 are bonded to the respective cuff ports 32 and 19 by conventional methods. The distal and proximal cuff inflation lines 30 and 31 extend from the cuff ports 32 and 19 in the lumen 17 along the inner wall of the cannula 22 to the proximal end 12 of the lumen 17 where they exit from inflation line ports 23. The cuff ring inflation lines 30 and 31 are bonded to the inner wall of the cannula 22 by conventional methods. The cuff ring inflation lines 30 and 31 are sealed at the inflation line ports 23 to stop any air leakage. The proximal ends 12 of the cuff ring inflation lines 30 and 31 are adapted to connect to a regulated air supply 34, which functions to alternately inflate or deflate the distal and proximal cuff rings 27 and 28.

Figure 4A:
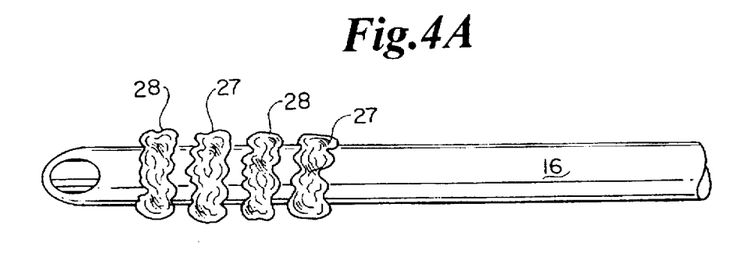
FIG. 4 illustrates three stages of inflation of the cuff rings.
Figure 4B:
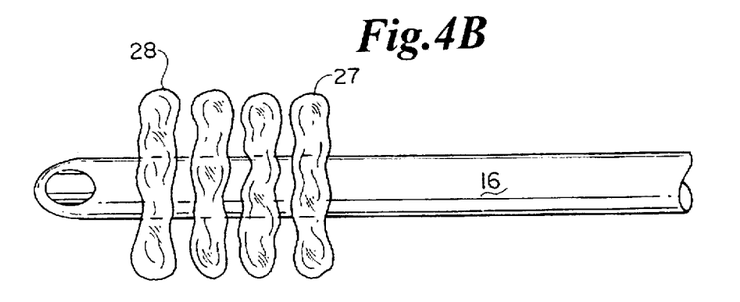
Figure 4C:
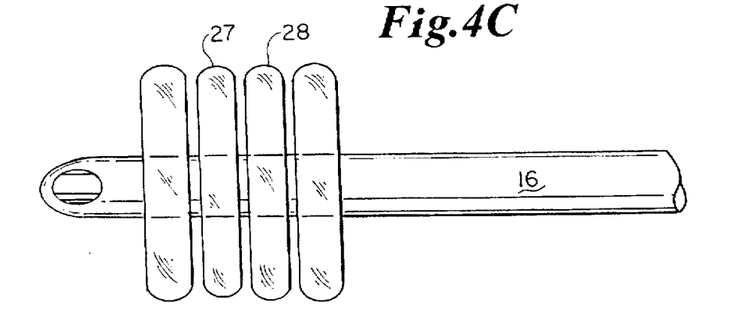
Figure 5A:
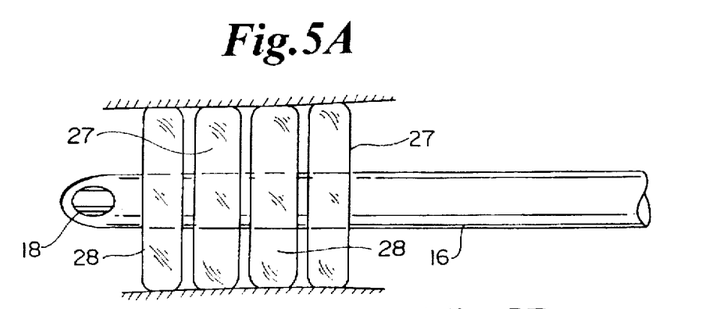
FIG. 5 depicts the sequence of inflation of the cuff rings.
Figure 5B:
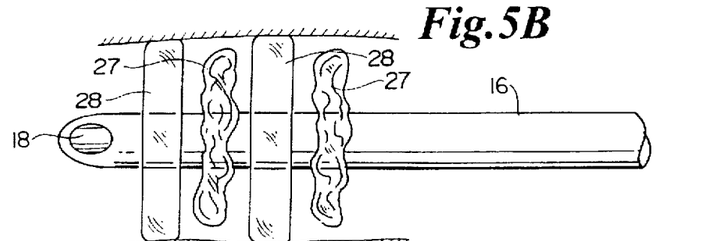
Figure 5C:
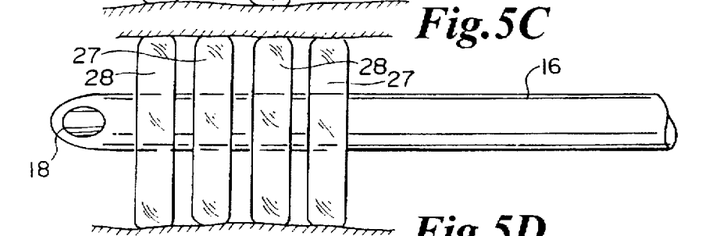
Figure 5D:
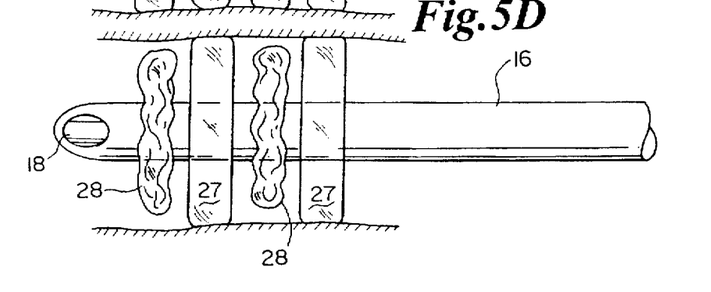

FIG. 4 illustrates the three stages of inflation of the present invention. FIG. 4A depicts the cuff rings 27 and 28 deflated, the state of the cuff rings 27 and 28 during insertion of the endotracheal tube 11 into the patient's trachea 35. FIG. 4B depicts the cuff rings 27 and 28 partially inflated. FIG. 4C depicts the cuff rings 27 and 28 fully inflated for maximizing the seal between the trachea 35 and the endotracheal tube 11.

FIG. 5 depicts a sequence of inflation of the cuff rings 27 and 28 of the present invention. Other sequences are just as efficacious, but the sequence of FIG. 5 is used for illustration. FIG. 5A begins with all the cuff rings 27 and 28 fully inflated. Full inflation of all of the cuff rings 27 and 28 provides maximum assurance of a full seal between the trachea 35 and the tube 11. However, the individual cuff rings 27 and 28 each have a surface area contacting the trachea such that any one of them alone will provide an adequate seal. It is preferred to have multiple cuff rings 27 and 28 inflated at any given time to provide adequate assurance that movement of the trachea 35 will not open small airways and compromise the seal momentarily. Inflation of more than one cuff ring 27 and 28 at a time is a prophylactic measure and allows the surface contact area of any one cuff ring 27 or 28 to be minimized, thereby reducing the area of the trachea that can potentially be damaged from the invasive introduction into the trachea of a foreign body-the cuff rings 27 and 28. FIG. 5B depicts the present invention with each of the distal cuff rings 28 partially deflated. The distal cuff rings 28 could be totally deflated, but partially deflation achieves the objective of relieving the trachea of the pressure exerted upon it by the distal cuff rings 28. It also allows faster deflation and inflation of the cuff rings 27 and 28. A further reason for partial deflation is to account for slight inaccuracies in the regulated air supply 34, which might cause excessive inflation of the cuff rings 27 and 28 resulting in damage to the cuff rings 27 and 28. FIG. 5C depicts the next sequence in the cycle of inflation and deflation. During this portion of the cycle, all of the cuff rings 27 and 28 are inflated providing for a maximal seal. Finally, FIG. 5D shows the proximal cuff rings 27 partially deflated. The cycle then repeats itself by full inflation of the proximal cuff rings 27 resulting in resumption of that part of the cycle depicted in FIG. 5A. Different sequences can be enabled by using a regulated air supply 34 designed to accommodate such a different sequence. Regulated air supplies 34 of a conventional design may also be modified to have variable sequences adjustable by either mechanical switching means or under microprocessor programmable control. For example, with a microprocessor under programmable control, the sequence of inflation and deflation can be randomly varied. The cuff rings 27 and 28 may each be individually connected to the regulated air supply 34 by separate inflation lines 30 or 31 and each cuff ring 27 and 28 inflated and deflated independent of any other cuff ring 27 and 28 and in a myriad of random sequences as determined by the computer program installed in the regulated air supply's 34 microprocessor memory. The length of inflation for any cuff ring 27 and 28 may be varied. The criteria for the length of inflation is to provide the maximum period of relief of the trachea from the pressure of the inflated cuff ring 27 and 28 and yet maintain an adequate seal.

Figure 6A:
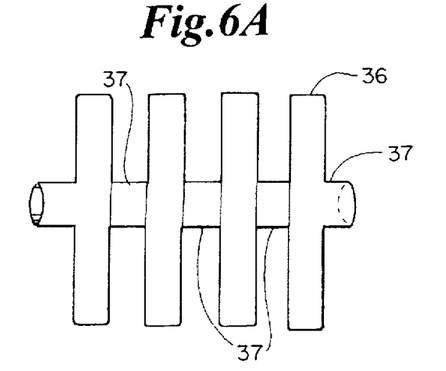
FIG. 6 is a detail of the cuff ring assembly and an illustration of the cuff ring assembly mounted on the cannula.
Figure 6B:
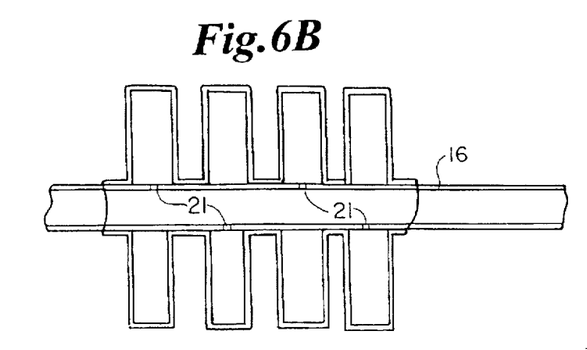

FIG. 6A is a detail of the cuff ring assembly 36 of the present invention. FIG. 6B is a detail of the ring cuff assembly 36 affixed to the cannula 16. As shown in FIG. 6A, all of the cuff rings 27 and 28 are constructed of a continuous film of polyvinyl chloride. The cuff ring assembly 36 is vacuum formed in a conventional molding process. The diameter of the cuff ring assembly shaft 37 is slightly larger than the diameter of the cannula 16 so that the cuff ring assembly shaft 37 may be slid over the cannula 16 and into position. The cuff ring assembly 36 is then bonded to the cannula 16 along the cuff ring assembly shaft 37 by conventional heat bonding techniques so that each cuff ring 27 and 28 has an air tight seal between it and the next cuff ring 27 and 28 and the outside wall 51 of the cannula 16. The cuff rings are positioned on the cannula 16 so that the cuff ports 21 are each located to provide an airway into an adjacent cuff ring 27 and 829. Alternatively, separate cuff rings 27 and 28 may be fabricated, positioned on the cannula 16, and separately bonded to the cannula 16.

FIG. 7 illustrates an alternate embodiment of cuff rings 27 or 28. Instead of cuff rings 27 or 28 oriented at an angle of ninety degrees to the longitudinal axis of the cannula 16, the cuff rings 27 or 28 are oriented at an acute angle to the longitudinal axis of the cannula 16, as shown partially inflated in FIG. 7B. In FIG. 7C cuff ring 27 or 28 is inflated to the normal maximum pressure of inflation. FIG. 7C illustrates the bending action of the alternate embodiment cuff rings 27 and 28 which more easily allows the cuff rings 27 or 28 to conform to various sizes and shapes of trachea. FIG. 7A shows the cuff rings 27 or 28 in an uninflated state. This alternate embodiment cuff ring 27 or 28 provides an in situ automatically deformable cuff that conforms to the contours and diameter of the various trachea encountered.

Figure 7A:
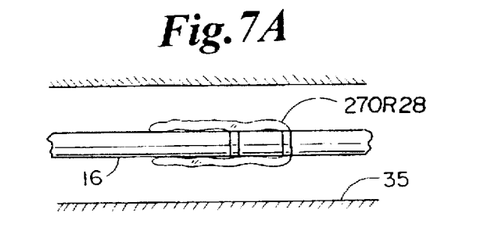
FIG. 7 presents alternate cuff ring embodiments in various states of inflation.
Figure 7B:
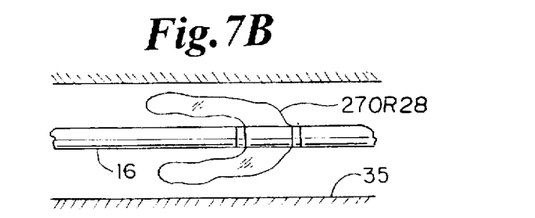
Figure 7C:
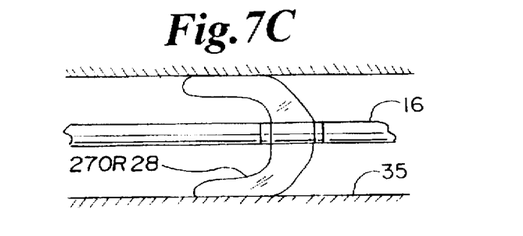
Figure 7D:
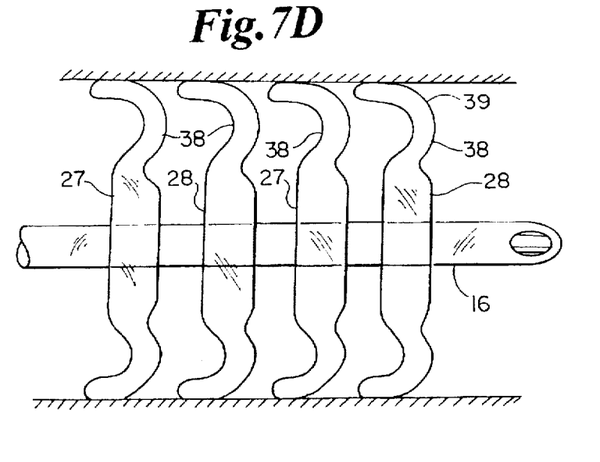

FIG. 7D illustrates yet another alternate embodiment of cuff ring 27 or 28. In this embodiment, the cuff rings are oriented at an angle of ninety degrees to the longitudinal axis of the cannula 16. However, the outer circumferential wall 39 of the cuff ring 27 or 28 that contacts the trachea 35 depends from the cuff ring 27 or 28 by thin wall cuff ring neck 38. The outer circumferential wall 39 is itself an extension of the thin wall cuff ring neck 38. The outer circumferential wall 39 is oriented parallel to the longitudinal axis of the cannula 16. If a smaller diameter trachea is encountered, the thin wall cuff ring neck 38 bends thereby allowing the outer circumferential wall 39 to move towards the longitudinal axis of the cannula 16. The bending allows the cuff ring 27 or 28 to accommodate varying diameter trachea and also variations in contours of trachea.

Figure 8:
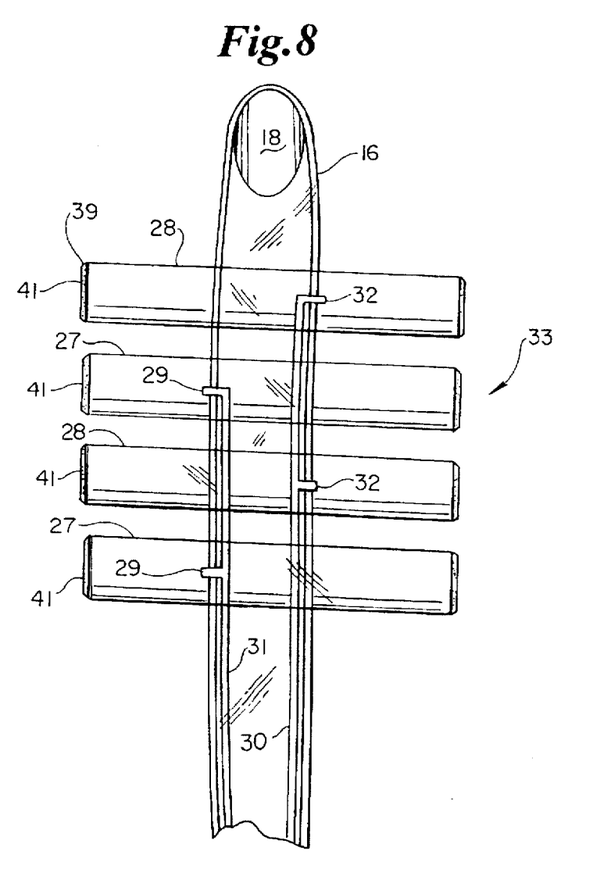
FIG. 8 is a representation of a cuff ring lubricant system.

FIG. 8 illustrates a cuff lubrication system for the endotracheal tube 11 of the present invention. Affixed to the outer wall 39 of at least one cuff ring 27 and 28 is a polymeric sponge material 41. The sponge material 41 is bonded to the outer wall 39 by conventional means. The sponge 41 has a continuous network of micropores in which a lubricant 40 is stored. The lubricant 40 is of a nature that is sterile, bio-compatible, absorbable by the tracheal mucosal membrane, and of a viscosity that will provide the required lubrication between the cuff rings 27 and 28 and the trachea 35. As the trachea 35 and the endotracheal tube 11 move relative to one another during the medical procedure in process the sponge 41 is slightly squeezed causing the lubricant 40 to be exuded from the sponge 41 onto the trachea 35 at the point of contact with the cuff rings 27 and 28. The continuous nature of the network of micropores in the sponge 41 acts as a reservoir of the lubricant 40 and yet allows only a small amount to continuously exude from the sponge 41. The micropore structure retains most of the lubricant 40 even when it is squeezed, only working its way through the continuous network of micropores with time. This allows a continuous lubricating action even during lengthy medical procedures. The periodic inflation and deflation of the cuff rings 28 and 29 contributes to the squeezing of the lubricant 40 out of the sponge 41, especially as the cuff rings 27 and 28 are once again inflated and pressed against the trachea 35.

Figure 9A:
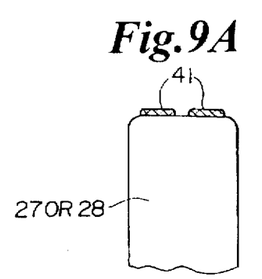
FIG. 9 is a representation of an alternate embodiment of a cuff ring lubricant system.
Figures 9B, 9C:
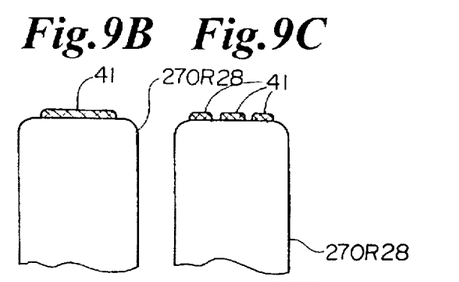
Figure 9D:
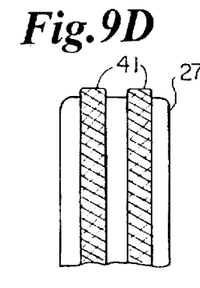
Figures 9E, 9F:
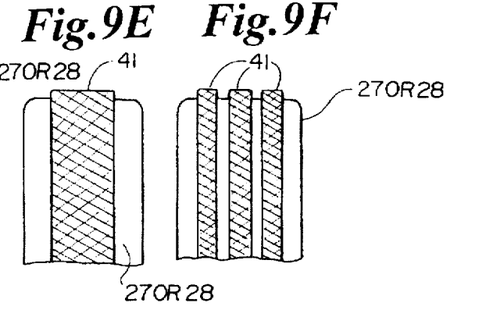

As shown in FIG. 8, the polymeric sponge 41 is affixed to the cuff rings 27 and 28 so that it fully encircles the cuff rings 27 and 28 about their outer wall 39 as well as over the entire width of the outer wall 39. However, an alternate embodiment of this lubricating system 33 provides for the outer wall 39 to have the sponge 41 affixed to only a portion of the cuff rings 27 and 28 either along their circumference or width and rely upon the natural migration of the lubricant 40 in the trachea 35 to lubricate other areas of the contact points of the cuff rings 27 and 28 and the trachea 35. FIG. 9 illustrates circumferential sponge 41 occupying less than all of the outer wall 39 of the cuff ring 27 or 28. FIG. 9A shows the sponge 41 in cross section and FIG. 9B shows a cuff ring 27 or 28 with various numbers of circumferential bands of sponges 41 in various widths.

The same concept of providing lubrication to ease the abrasion of the trachea 35 from movement of the endotracheal tube 11 relative to the trachea 35 is applicable to the conventional cuff 19 embodiment previously shown in FIG. 1. The concept and method of operation of the lubricating action is the same as for the cuff rings 27 and 28, except that the sponge 41 is a single sponge rather than a series of individual sponges attached to multiple cuff rings 27 and 28. As with the polymeric sponge 41 of cuff rings 27 and 28, the sponge 41 for the cuff 19 surrounds the entire outer wall 39 of the cuff 19. An alternate embodiment of this lubricating sponge system for conventional cuff 19 is to have the sponge 41 cover only a portion of the outer wall 39.

Figure 10:
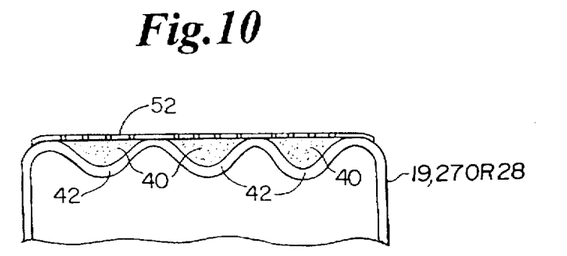
FIG. 10 presents an alternate system of lubrication of a cuff or a cuff ring using lubrication depressions.

Another system of lubrication of the conventional cuff 19 shown in FIG. 1 or of cuff rings 27 and 28 is depicted in FIG. 10. Lubricating depressions 42 are formed in the cuff 19 or the cuff rings 27 and 28. These depressions 42 are covered over to form a smooth continuous surface with the outer wall 39 of the cuff 19. The same material is used to cover the lubricating depression 42 as is used to form the cuff 19 or the cuff rings 27 and 28. The lubricant 40 extends around the entire circumference of the cuff 19 or the cuff rings 27 and 28. The outer wall 39 of the lubricating depression 42 contains a plurality of perforations 52 of a size to allow the slow controlled exudation of the lubricant 40 contained in the lubricating depression 42 upon compression against the trachea 35 by inflation of the cuff 19 or cuff rings 27 and 28. The lubricating depressions 42 are spaced along the length of the cuff 19 or cuff rings 27 and 28 in a number adequate to lubricate the entire tracheal area in contact with the cuff 19 or cuff rings 27 and 28. The lubricant 40 migrates to a degree that allows the lubricant 40 to move from the area of the lubricating depression 42 to the area of the outer wall 39 of the cuff 19 or cuff rings 27 and 28.

The foregoing description is illustrative of the invention described herein and should not be used to unduly limit the scope of the invention or the claims. Since many embodiments and variations can be made while remaining within the spirit and scope of the invention, the invention resides wholly in the following claims.

What is claimed is:

1. A method of maintaining a constant air seal between an endotracheal and a trachea and of minimizing damage to the tracheal wall due to the constant pressure of the air seal means against the tracheal wall comprising the steps of:

a) inserting an endotracheal tube into the trachea;

b) surrounding a portion of the endotracheal tube in the trachea with a plurality of deflated cuff rings, said cuff rings capable of being inflated and deflated;

c) inflating at least one of the cuff rings so that at least one inflated cuff ring maintains an air seal between the tracheal wall and the endotracheal tube;

d) inflating at least one of the cuff rings not inflated in previous step (c);

e) deflating the cuff rings inflated in step (c);

f) repeating successively steps (c) through (e) in the same order; and g) then deflating all cuff rings and removing the endotracheal tube from the trachea.

2. A method of maintaining a constant air seal between an endotracheal tube and a trachea and of minimizing damage to the trachea due to constant pressure of the air seal means against the trachea comprisng the steps of:

a) inserting an endotracheal tube into the trachea;

b) surrounding a portion of the endotracheal tube in the trachea with a plurality of deflated cuff rings, said cuff rings capable of being separately inflated and deflated;

c) inflating one of the cuff rings so that the inflated cuff ring maintains an air seal between the trachea and the endotracheal tube;

d) inflating one of the other cuff rings not inflated in step c) so that the other inflated cuff ring maintains an air seal between the trachea and the endotracheal tube;

e) deflating the cuff ring inflated in step c);

f) repeating step c);

g) deflating the cuff ring inflated in step d);

h) repeating successively steps d) through g) in the same order; and g) then deflating all cuff rings and removing the endotracheal tube from the trachea.

3. A method of maintaining a constant air seal between one of a first and a second cuff rings and a trachea while minimizing damage to the trachea due to constant pressure of the air seal against the trachea by:

a) inserting a cannula into the trachea;

b) providing a plurality of cuff rings surrounding a distal portion of the cannula in the trachea, at least the first and second of said cuff rings capable of being separately inflated and deflated independently of each other and independently of any other of said cuff rings;

c) inflating the first cuff ring, so that the first cuff ring maintains an air seal between the trachea and the cannula;

d) inflating the second cuff ring, so that the second cuff ring maintains an air seal between the trachea and the cannula;

e) deflating the first cuff ring;

f) repeating step c);

g) deflating the second cuff ring; and h) repeating successively steps d) through g).

* * * * *